US012653569B2

(12) United States Patent
Hacker

(10) Patent No.: US 12,653,569 B2
(45) Date of Patent: Jun. 16, 2026

(54) SHARPS BLADE EJECTOR MECHANISM

(71) Applicant: Nano Surgical, LLC, Delray Beach, FL (US)

(72) Inventor: Steven M. Hacker, Delray Beach, FL (US)

(73) Assignee: Nano Surgical Inc., Delray Beach, FL (US)

( * ) Notice: Subject to any disclaimer, the term of this patent is extended or adjusted under 35 U.S.C. 154(b) by 0 days.

(21) Appl. No.: 18/968,170

(22) Filed: Dec. 4, 2024

(65) Prior Publication Data

US 2026/0151156 A1     Jun. 4, 2026

(51) Int. Cl.
A61B 17/3217     (2006.01)
A61B 17/3215     (2006.01)

(52) U.S. Cl.
CPC ...... A61B 17/3217 (2013.01); A61B 17/3215 (2013.01)

(58) Field of Classification Search
CPC ........................ A61B 17/3217; A61B 17/3215
USPC .................................................. 206/355, 356
See application file for complete search history.

(56) References Cited

U.S. PATENT DOCUMENTS

| | | | | |
|---|---|---|---|---|
| 5,330,494 A | * | 7/1994 | van der Westhuizen | ................... A61B 17/3211 30/2 |
| 5,556,409 A | * | 9/1996 | Haining | ............. A61B 17/3211 30/162 |
| 2004/0158269 A1 | * | 8/2004 | Holman | ............. A61B 17/3213 606/167 |
| 2005/0203555 A1 | * | 9/2005 | Griffin | ............... A61B 17/3215 606/167 |
| 2010/0305593 A1 | * | 12/2010 | Inzero | ................ A61B 17/3215 606/167 |

* cited by examiner

*Primary Examiner* — Jacob K Ackun
(74) *Attorney, Agent, or Firm* — Quantum Patent Law Firm; Seongyoune Kang

(57)     ABSTRACT

A sharps blade ejector mechanism for safely removing used sharps blade from various surgical instrument handles without the need for using additional blade remover devices, needle holder instruments, or physical contact with the sharps blade is disclosed. The sharps blade ejector mechanism comprises a specifically configured handle in coordination with a molded sharps blade unit. The handle may be illuminated. The sharps blade may be a scalpel blade, a needle, a probe, a dissector, an elevator, a saw blade, a retractor or a hook.

23 Claims, 5 Drawing Sheets

SHARPS BLADE EJECTOR MECHANISM

FIELD OF THE INVENTION

The invention relates to a sharps blade ejector mechanism for safely removing used sharps blades from various surgical instrument handles without the need for physical contact with the sharps blade. The sharps blade ejector mechanism comprises a specifically configured handle in coordination with a molded sharps blade unit. The handle may be illuminated. The sharps blade may be a scalpel blade, a needle, a probe, a dissector, an elevator, a saw blade, a retractor or a hook.

BACKGROUND OF THE INVENTION

Typical surgical knives or scalpels comprise a disposable scalpel blade which is removably attached to a scalpel handle. Scalpel handles are known to comprise an elevated boss (also called a universal blade fitting) at one end of a bayonet holder to which a scalpel blade can be removably attached. Typically a scalpel blade is provided with a keyed slot for attachment to the universal blade fitting. In attaching the scalpel blade to the universal blade fitting, the keyed slot portion of the scalpel blade must be slightly deformed, or flexed, to force it into a groove on the universal blade fitting and provide a snap fit. The scalpel blade can be removed from the universal blade fitting by handling one end of the scalpel blade with surgeon's needle holders, elevating the universal blade fitting and pushing the scalpel blade in a forward direction as it slides off the universal blade fitting.

Injury is very common at any point of attaching a scalpel blade to or removing a contaminated used scalpel blade from a scalpel handle. Injury with a contaminated scalpel blade is serious to the injured given the risks of blood borne pathogens.

To reduce the possibility of injury in the contaminated scalpel blade removal process, medical personnel must be able to safely and easily remove contaminated used scalpel blades from a scalpel handle without injuring themselves in the process. Additionally, medical personnel must be able to accurately account for all contaminated scalpel blades that are used and removed during surgery to ensure that no contaminated scalpel blades remain in the patient or in the operating room. Further, medical personnel must be able to safely dispose of contaminated scalpel blades so that the used scalpel blades cannot accidentally cause injury to others. "OSHA's bloodborne pathogens standard prohibits the bending, recapping or removal of a contaminated needle or other contaminated sharp unless the 'employer can demonstrate that no alternative is feasible or that such action is required by a specific medical or dental procedure.' [29 CFR 1910.1030(d)(2)(vii)(A)]. Therefore, using fingers to remove a used scalpel blade does not meet the requirements of the standard. In situations where an employer has demonstrated that the use of a scalpel with a reusable handle is required by a specific medical or dental procedure or that no alternative is feasible, blade removal must be accomplished through the use of a mechanical device or a one-handed technique [29 CFR 1910.1030(d)(2)(vii)(B)]," available on Nov. 17, 2024 at <<https://www.osha.gov/laws-regs/standardinterpretations/2008-11-21-0>>.

There are 4 main types of prior art that exist to prevent users from accidental contact with sharp blades. The 4 areas involve devices where 1) the sharp blade is retracted into the body of the device; 2) the device is a disposable or single use application, where the entire sharp blade with the handle is not reused; 3) a device that moves in a non-linear fashion to cover the sharp blade while it is not in use; and 4) a device that removes a detachable sharp blade from the handle of the device.

In the fourth type of prior art, one option is to insert the scalpel handle with the loaded and used contaminated scalpel blade into a "blade remover" apparatus that is designed to remove the contaminated and used scalpel blade from the scalpel handle. The limitations of this procedure include the cost of the "blade remover" apparatus; the need for access to a "blade remover" apparatus in every hospital room, OR, ER and in immediate proximity to where surgery is performed so that surgical personnel are not walking very far with a contaminated scalpel blade on a scalpel handle; and finally fit limitations as certain "blade remover" apparatuses only work with certain scalpel handle shapes and sizes. Once the contaminated scalpel blade is removed, the scalpel handle may then be cleaned and sterilized and used again in a subsequent surgical procedure, by attaching a new scalpel blade to the scalpel handle. For example, U.S. Pat. No. 4,318,473 to Sandel, incorporated herein by reference, discloses a scalpel blade removal and disposal device in which a blade and handle are inserted through a guide so that the rear of the scalpel blade is in contact with two shoulders, and the forward end of the scalpel blade is under an abutment. To remove the scalpel blade from the handle, the scalpel handle is urged downward against the shoulders, which bows the scalpel blade, thereby disengaging the rear end of the scalpel blade from the rear face of the raised portion of the scalpel handle. The scalpel handle is then pulled from guide means while a wall and stop restrain the scalpel blade, thereby disengaging the scalpel blade from the scalpel handle.

Other devices that fall into the $4^{th}$ type of prior art involve handling of the sharp blade prior to its inclusion into some protective cover, increasing the chance of accidental puncture. For example, Herbert et al in U.S. Pat. No. 5,868,771 issued on Feb. 9, 1999, Newman et al in U.S. Pat. No. 6,626,925 issued on Sep. 30, 2003 and van der Westhuizen et al in U.S. Pat. No. 5,330,494 disclose a procedure of attaching a sharp blade to a handle and then attaching a sliding blade guard. Once the sharp blade is used, it can be removed from the handle along with the guard. Herbert uses existing style surgical handles, while van der Westhuizen and Newman use a unique handle that is modified at the distal end of the handle nearest the sharp blade, to receive the guard. Both devices require the user to load the sharp blade onto the handle, requiring the unguarded sharp blade to be handled by those that the device is designed to protect, and often those people are wearing gloves which will reduce tactile feel.

In the approach disclosed by Noack in U.S. Pat. No. 5,312,429, a unique sharp blade with an opposed tang is removed by a sliding blade release element when the element is slid down the handle toward the sharp blade. This is a two-handed operation involving two separate pieces. In the sliding of the element, if one's hand slips from the element it risks being cut by the exposed sharp blade. Also, the sharp blade is without direction or restraint when released from its location on the handle and it could travel anywhere in the operating room.

Cartridge types highlighted by U.S. Pat. No. 7,207,999 to Griffin et al disclose the use of a cartridge that contains a sharp blade for a scalpel. The cartridge doubles as a shield when it is retracted over the handle after the attachment of the sharp blade to the tang of the handle. Each cartridge is unique to a particular style of sharp blade and requires a two-handed operation to remove and attach the sharp blade. This extra cartridge material creates costly waste, requires extra steps by the surgeon and changes the overall size and surgeon's fell of the handle when in use.

U.S. Pat. No. 7,172,611 issued to Harding et al discloses another cartridge that is required to use a special sharp blade with "non-arcuate" holes which increase the cost and decreases its effectiveness to be used with a broad range of access. All disclosed cartridge style scalpels use the removal of the cartridge that contains the sharp blade as the means for sharp blade removal. Though safe, these devices are limited by requiring unique cartridges to hold the wide variety of sharp blades available.

Another adaptation of this concept is found a series of patents from Jolly et al, U.S. Pat. Nos. 5,827,309, 5,752,968 and 5,792,162. The Jolly patents disclose a sharp blade remover which first removes the tang of the sharp blade from the post into a notch on the sliding guard. The "guard can be advanced distally to force blade from blade carrier". The built-in stresses mentioned above are increased with a forcible removal of the sharp blade with the sliding guard, increasing the chance for the sharp blade to be misdirected about the operating room.

Gharibian in U.S. Pat. No. 5,527,329 and Cohn et al in U.S. Pat. No. 5,938,676 disclose the use of a cartridge system whereby the sharp blade is placed into a cartridge which is then encased by a guard prior to its placement onto the handle. The sharp blade is guarded during assembly. Each handle is uniquely designed to receive cartridges and shields. Cohn et al in U.S. Pat. No. 5,941,892 combines prior art by incorporating the cartridge concept that is "removably retained within the cavity" in the handle. This is a safe alternative but uses unique handles. All of this prior art requires the use of two hands to safely operate the device which is at odds with current FDA and OSHA compliance rules.

In one last type of prior art, a guard is placed around a stationery blade. Applications of a more complex nature are found in Abidin et al in U.S. Pat. Nos. 5,662,669 and 5,569,281, Jolly et al in U.S. Pat. No. 5,741,289, Matwijcow in U.S. Pat. No. 5,207,696 and Dolgin et al in U.S. Pat. No. 5,071,426. Matwijcow discloses a rack and pinion system for movement of the guard over the blade which causes a reverse sequence of logic, as the user needs to pull back to move the guard forward. This could be confusing in the fast-paced operating room where several different type of devices might be used at once. Dolgin also uses a "linkage system" to extend the blade guard "over a substantially greater distance than the distance which the surgeon's fingers move in operating the actuating mechanism". This is complex and an expensive concept using unique handles which requires manual loading of the blades onto the handle. Jolly provides for both linear actuation of the guard along with a rotational movement of the guard and blade away from the handle for cleaning purposes. This device is complex and expensive to manufacture and use. The Abidin '281 patent discloses a guard which "comprises an inverted U-shaped channel member telescopically mounted within the hollow handle for sliding movement therein". It is held in position by exposed an exposed pin which would be in the way of the surgeon's hands and could be accidentally triggered to move.

Abidin '669 is another internally guided blade guard with a unique handle prior art. This prior art combines a blade guard and a blade ejector but details the need for two handed operations to remove the blade. Particular to the prior art, the blade is not restrained after it is removed from the handle, and as described above, there is a considerable amount of tension on the blade.

U.S. Pat. No. 8,156,653 to Austria discloses a top rail mounted scalpel with three basic segments. That invention requires the use of two hands to eject the sharp blade and the sharp blade becomes trapped in the shield, requiring the use of another action by the user to get rid of the sharp blade.

Though only 7% of the population are considered left-handed, over 15% of all surgeons are left-handed according to an article in the British Medical Journal published in 2005, which found that left-handed surgeons are forced to use right-handed devices causing a greater incident of accidental punctures from sharps. Additionally, the adoption rate of safety scalpel handles is projected at less than 10% likely because of the extra manual steps or the physical change to the scalpel itself affecting the surgeon's visibility, or ergonomic comfort. See DeGirolamo K M, Courtemanche D J, Hill W D, Kennedy A, Skarsgard E D. Use of safety scalpels and other safety practices to reduce sharps injury in the operating room: what is the evidence? *Can J Surg.* 2013; 56(4):263-269. doi:10.1503/cjs.003812.

SUMMARY OF THE INVENTION

The scalpel blade ejector mechanism of the invention provides a safe effective, cost and time saving and convenient way for removing used contaminated scalpel blades from scalpel handles without the need to physically touch the scalpel blade when attaching to a handle and without the need to use a needle holder instrument to grab the scalpel blade to remove it from a scalpel handle, which minimizes the risk of injury, while being flexible and simple to operate. The scalpel blade ejector mechanism does not require any special apparatus such as the current "blade remover" apparatuses that are required to be accessible in every hospital room, OR, ER, clinic, office procedure room and in immediate proximity to where surgery is performed and that have "fit" limitations as certain "blade remover" apparatuses only work with certain scalpel handle shapes and sizes. Additionally, the scalpel blade ejector mechanism reduces costs and improves access by taking advantage of already ubiquitous placement of "red box" sharps containers deployed for used needle and sharp blade disposal. The scalpel blade ejector mechanism of the invention works "hands-free" thus overcoming OSHA's bloodborne pathogens standards at 29 C.F.R. 1910.1030 regarding the use of fingers to remove used scalpel blades.

The scalpel blade ejector mechanism according to one embodiment of the invention is designed to both engage and disengage to reversibly attach and detach then eject a molded scalpel blade unit from a scalpel handle upon depression of a switch without the need to physically touch the scalpel blade, where the scalpel blade unit comprises a scalpel blade and is over molded with plastic or other material as a unit and in a shape that enables mating with the scalpel handle. In one embodiment, the scalpel blade unit is disposable. In one embodiment, the scalpel blade unit is light transmissible. In one embodiment, the scalpel handle is reusable. Finally, the scalpel blade ejector mechanism and/or the scalpel handle can enable light transmission through and all around the scalpel blade for illumination during use.

The scalpel blade ejector mechanism can be used for a scalpel blade unit to which any sharp or surgical instrument device can be attached and then attached to a handle, whether light transmitting or not, particularly in the medical and surgical field, and may include needles, probes, dissectors, elevators, saw blades, hooks and other sharp tip instruments. While the invention is described in terms of a scalpel blade, it can be used for any type of sharps instrument and handle.

The scalpel blade ejector mechanism allows for contaminated and used scalpel blades to be ejected directly from a scalpel handle into a "red box" sharps container for disposal. The scalpel blade ejector mechanism enables insertion of a molded scalpel unit onto a scalpel handle without handling of the scalpel blade by medical personnel.

Additionally, the scalpel blade ejector mechanism of the invention can be used by both left-handed and right-handed operators.

BRIEF DESCRIPTION OF THE DRAWINGS

The foregoing features of the invention will become more readily understood by reference to the following detailed description when taken in conjunction with the accompanying drawings, wherein.

DETAILED DESCRIPTION OF THE INVENTION

The scalpel blade ejector mechanism of the invention provides a device and process for safe removal of a contaminated scalpel blade from a scalpel handle. The scalpel blade ejector mechanism can be used by left-handed and right-handed personnel and allows for ejection of a contaminated scalpel blade directly into a "red-box" sharps container for disposal as is currently required under applicable OSHA regulations and practices.

Figure 1:
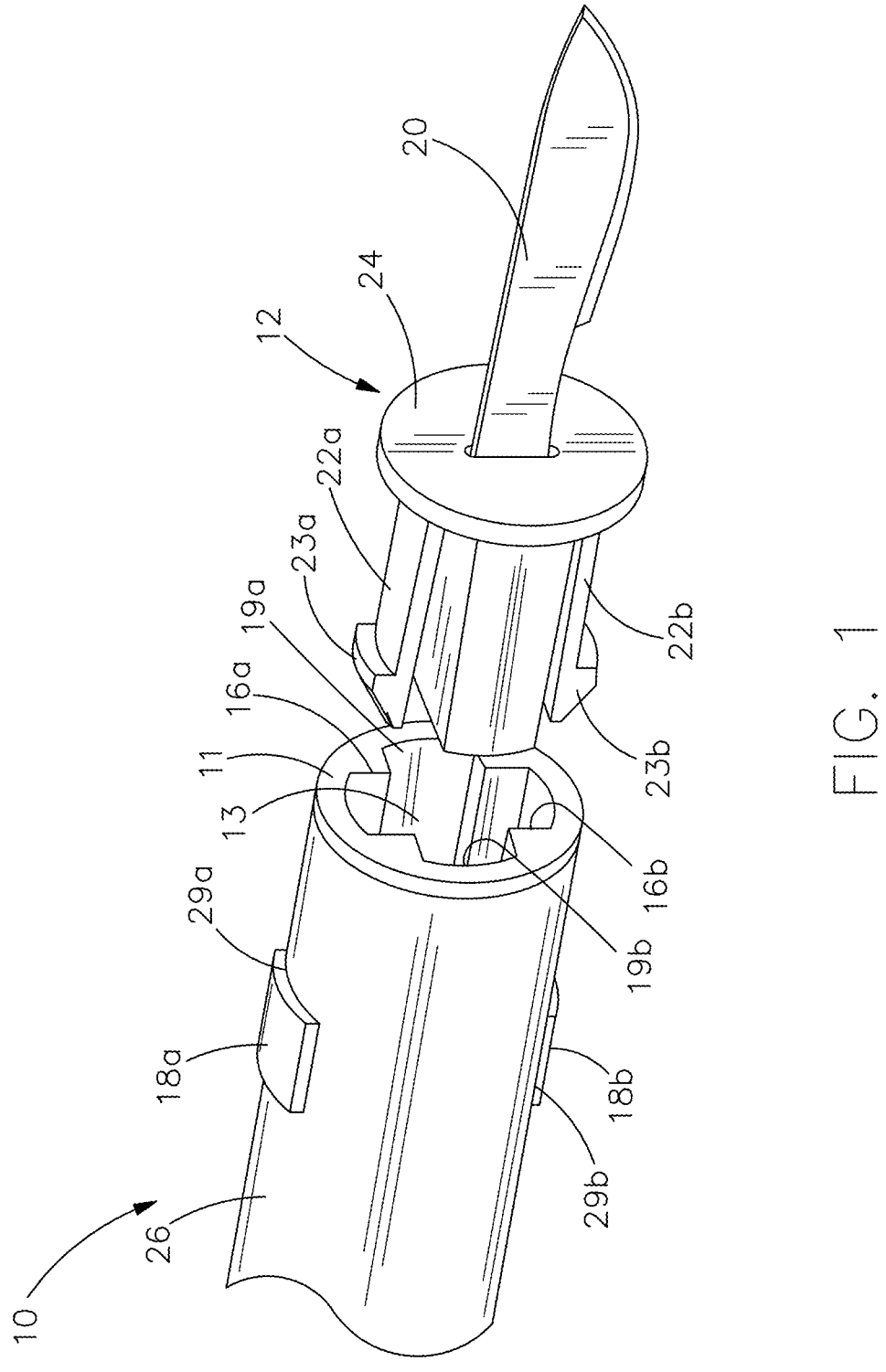
FIG. 1 is a perspective view of a receiving end of a scalpel blade ejector mechanism comprising a scalpel handle and a scalpel blade ejector unit according to one embodiment of the invention.
Figure 2:
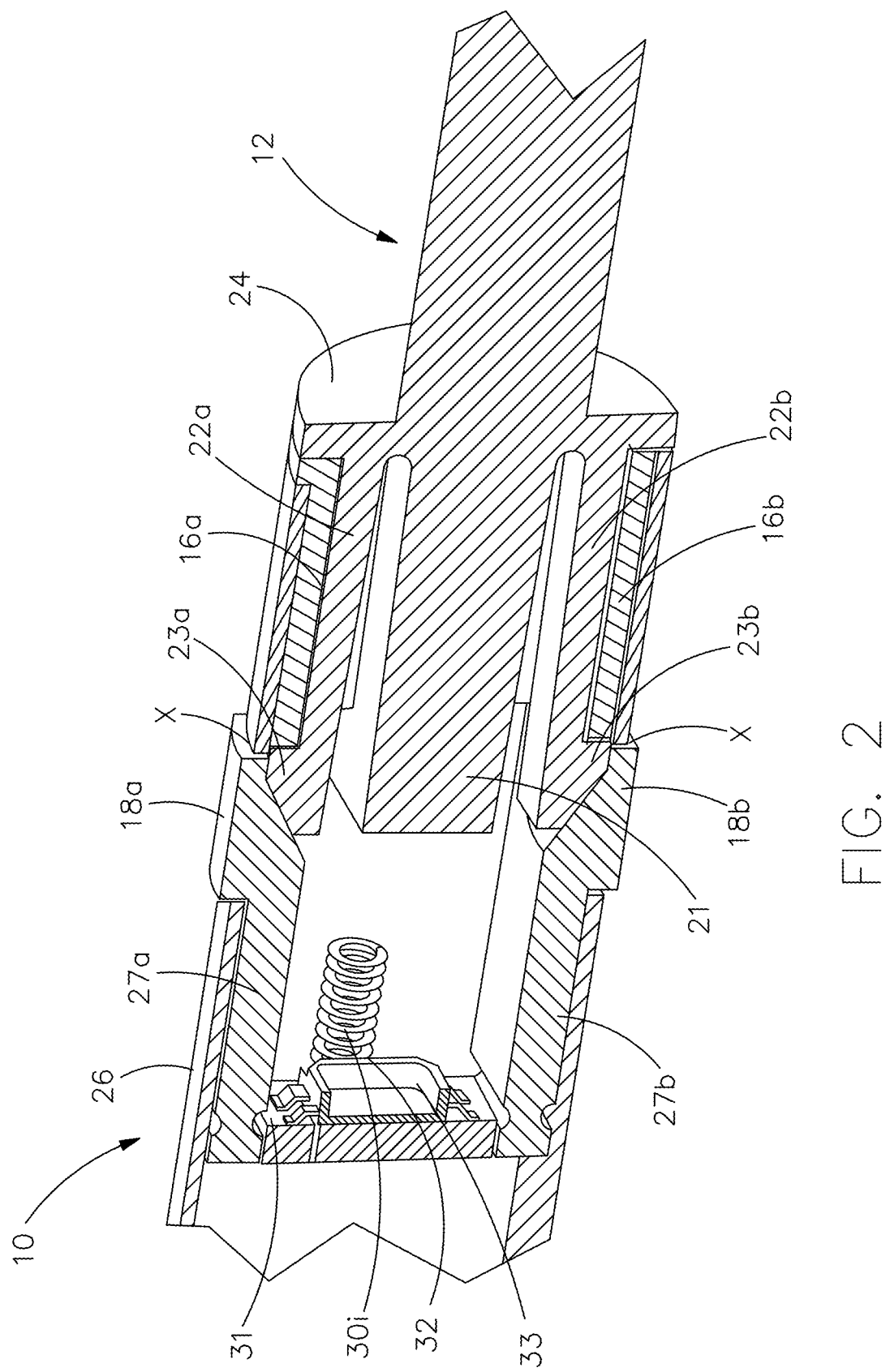
FIG. 2 is a cross-section view of the receiving end of the scalpel handle with the scalpel blade unit of FIG. 1.

The scalpel blade ejector mechanism depicted in FIGS. 1 and 2 comprises two components. The first component is a hollow scalpel handle 10 and the second component is a molded scalpel blade unit 12.

As seen in FIGS. 1 and 2, scalpel handle 10 comprises surface 26 which defines cavity 13 and has a proximal end 11. Scalpel handle 10 comprises an upper engagement portion 16a and a lower engagement portion 16b disposed on opposing sides of the interior of surface 26 and that extend along inside of scalpel handle 10 from proximal end 11 to a position X distal from proximal end 11. Scalpel handle 10 further comprises upper engagement release arm 27a and lower engagement release arm 27b disposed on opposing sides of the interior of surface 26 and that extend along the inside of surface 26 and terminate at upper release button 18a and lower release button 18b, each of which extends through upper release hole 29a and lower release hole 29b through surface 26 of scalpel handle 10 to the exterior environment. Each of upper release hole 29a and lower release hole 29b extends beginning at position X along surface 26 to a point distal from position X and proximal end 11. Upper engagement release arm 27a and lower engagement release arm 27b are flexed inwardly into cavity 13 by depression of upper release button 18a and lower release button 18b. Upper engagement release arm 27a comprises upper engagement release button 18a at its end proximal to upper engagement portion 16a which extends downward from surface 26 and comprises an angled face angling downward away from proximal end 11. Lower engagement release arm 27b comprises lower engagement release button 18b at its end proximal to lower engagement portion 16b and comprises an angled face angling downward away from proximal end 11. Cavity 13 further comprises side passages 19a, 19b disposed at 90 degrees on either side of upper engagement portion 16a and lower engagement portion 16b. One or more springs $30_i$ are attached to a surface 31 that is disposed in cavity 13 such that the one or more springs $30_i$ are oriented along the longitudinal axis of scalpel handle 10. One or more springs 30 may be positioned within cavity 13 as necessary or desired to accommodate other components within cavity 13. In one embodiment, one or more springs $30_i$ are disposed off-center of a longitudinal axis of scalpel handle 10 to permit circuitry and illumination units 33.

Scalpel blade unit 12 comprises scalpel blade 20 in permanent attachment to end unit 24 on a side of end unit 24 distal from scalpel handle 10. Scalpel blade unit 12 may comprise a removable guard (not shown) that can be removed after scalpel blade unit 12 is attached to scalpel handle 10. Central arm 21 extends from the side of end unit 24 proximal to scalpel handle 10 and mates inside of side passages 19a, 19b in cavity 13 of scalpel handle 10. Upper arm 22a and lower arm 22b extend perpendicularly from the side of end unit 24 proximal to scalpel handle 10. Upper arm 22a comprises an upper arm shoulder 23a and lower arm 22b comprises a lower arm shoulder 23b. Upper arm shoulder 23a extends upward away from central arm 21 and comprises an angled face angling downward toward central arm 21 on the end of upper arm 22a proximate scalpel handle 10. Lower arm shoulder 23b extends downward away from central arm 21 and comprises an angled face angling upward toward central arm 21 on the end of lower arm 22b proximate scalpel handle 10. Upper arm 22a and lower arm 22b are flexibly attached to end unit 24. Upper arm 22a and lower arm 22b mate inside of upper engagement portion 16a and lower engagement portion 16b in cavity 13 of scalpel handle 10.

Upon operation, personnel inserts central arm 21, upper arm 22a and lower arm 22b of scalpel blade unit 12 into cavity 13 of scalpel handle 10. Each of upper arm 22a and lower arm 22b have a length longer than upper engagement portion 16a and lower engagement portion 16b. Upper arm 22a and lower arm 22b are inserted into cavity 13 along engagement portion 16a and lower engagement portion 16b wherein upper arm 22a and lower arm 22b flex inwardly due to forces exerted by shoulders 23a, 23b as they travel along engagement portion 16a and lower engagement portion 16b. Once shoulders 23a, 23b have traveled past the ends of upper engagement portion 16a and lower engagement portion 16b that are distal from proximal end 11, the forces exerted by shoulders 23a, 23b are released, causing the angled faces of upper arm and lower arm shoulders 23a, 23b to mate with the angled faces of upper and lower engagement release arms 27a, 27b. Central unit 21 engages with one or more springs $30_i$. In one embodiment, central unit 21 engages with a spring block 32 which directly engages with the one or more springs $30_i$. In another embodiment, central arm 21 engages directly with one or more springs 30ᵢ, and as scalpel blade unit 12 is inserted into cavity 13, the one or more springs 30ᵢ are displaced from equilibrium. Upper engagement portion 16a and lower engagement portion 16b prevent upper arm and lower arm shoulders 23a, 23b from traveling toward proximal end 11 due to the spring force created in springs 30 as they are held in a displacement condition by surface 31.

To release scalpel blade unit 12 from scalpel handle 10, personnel presses upper engagement release button 18a and lower engagement release button 18b inward toward cavity 13. This causes the angled faces of upper and lower engagement release arms 27a, 27b to press down on the angled faces of upper arm and lower arm shoulders 23a, 23b such that upper arm and lower arm shoulders 23a, 23b are no longer engaged with the ends of upper and lower engagement portions 16a and 16b. This releases the spring force in springs 30ᵢ, causing scalpel blade unit 12 to disengage from scalpel handle 10, and whereupon scalpel blade unit 12 can be ejected directly into a disposable box.

Figure 3:
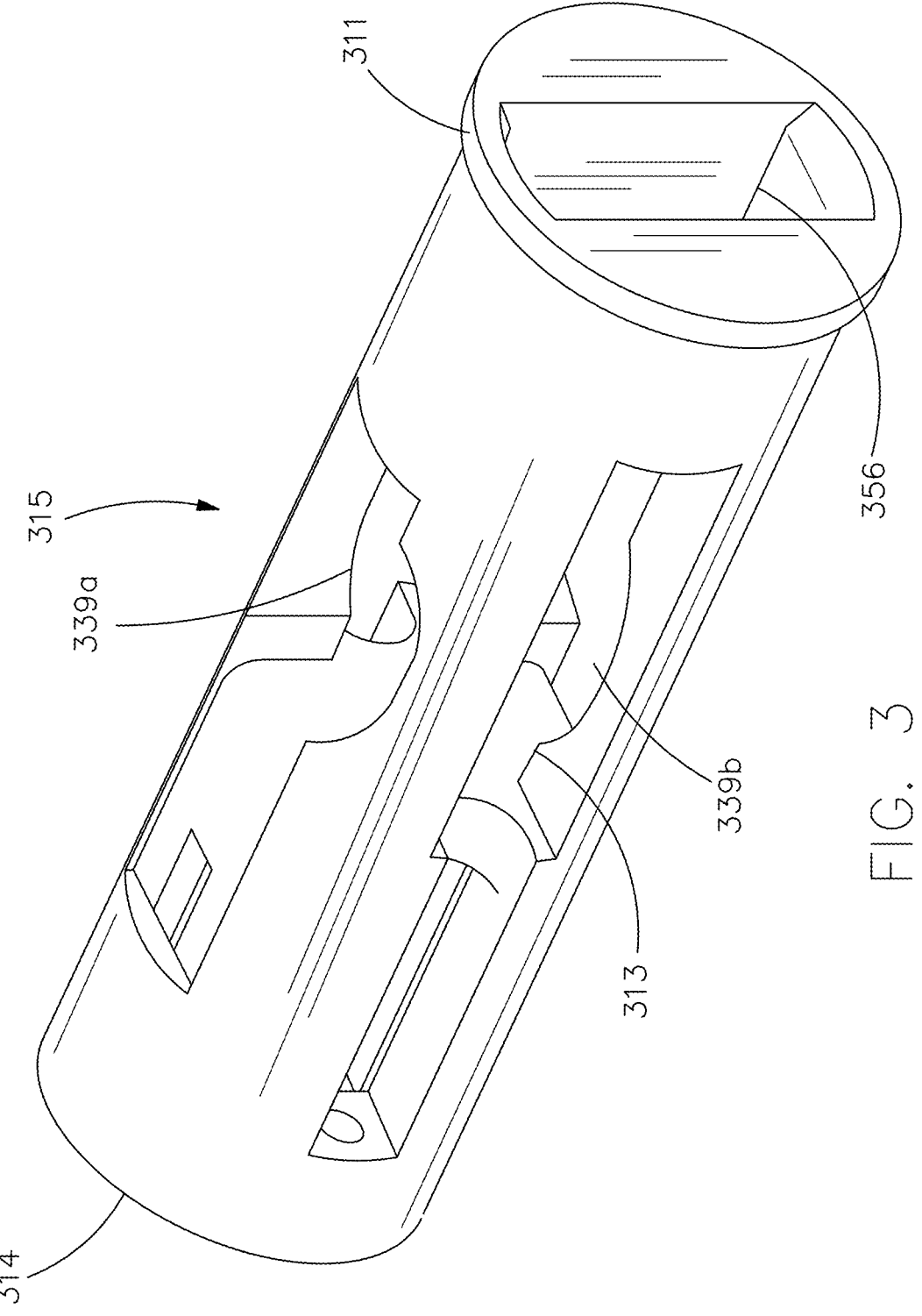
FIG. 3 is a perspective view of one embodiment of the invention showing an internal housing that can be inserted into a hollow handle.
Figure 4:
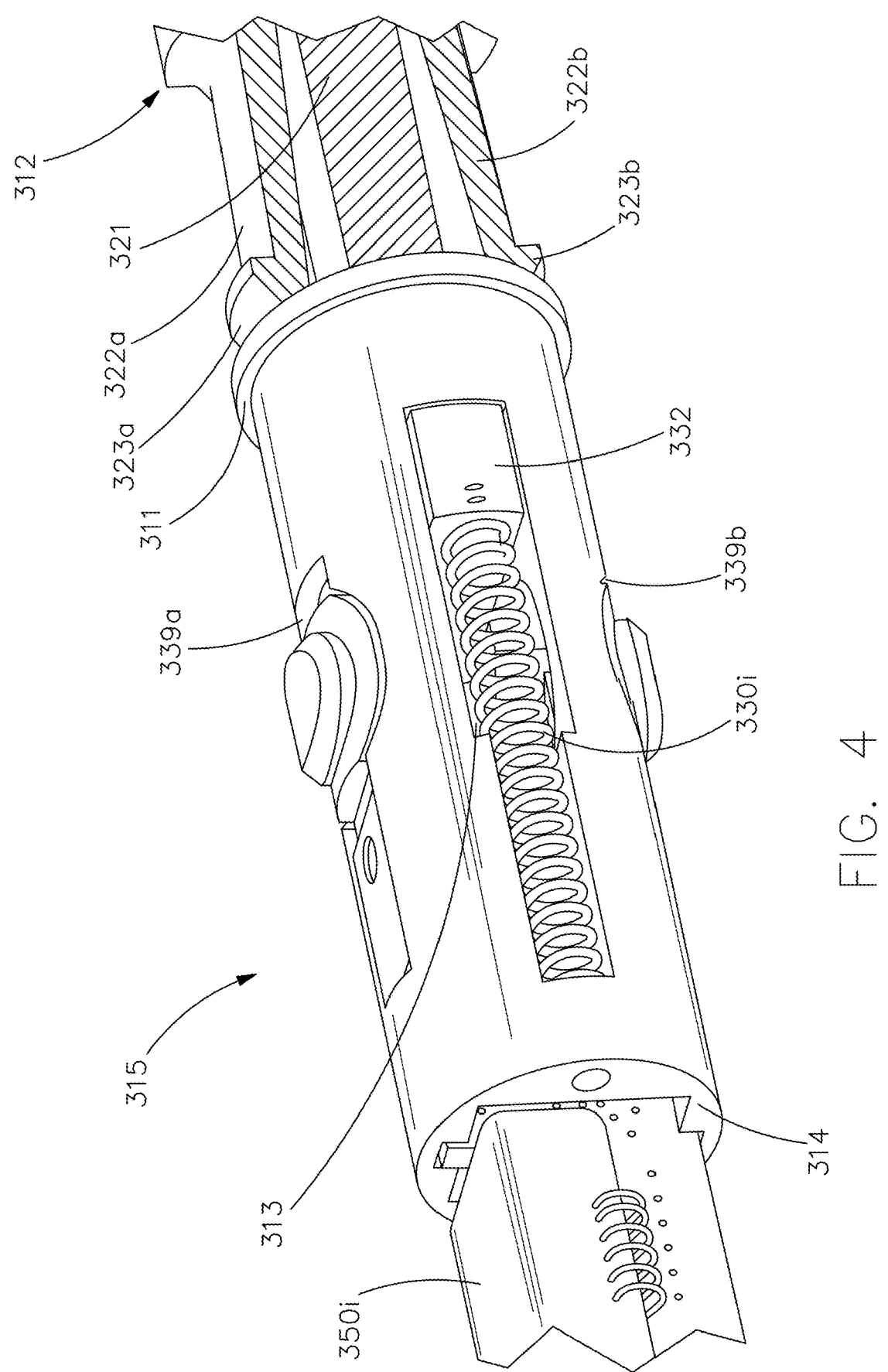
FIG. 4 is a perspective partial view of an interior housing unit, a sharps blade unit and components according to one embodiment of the invention.
Figure 5:
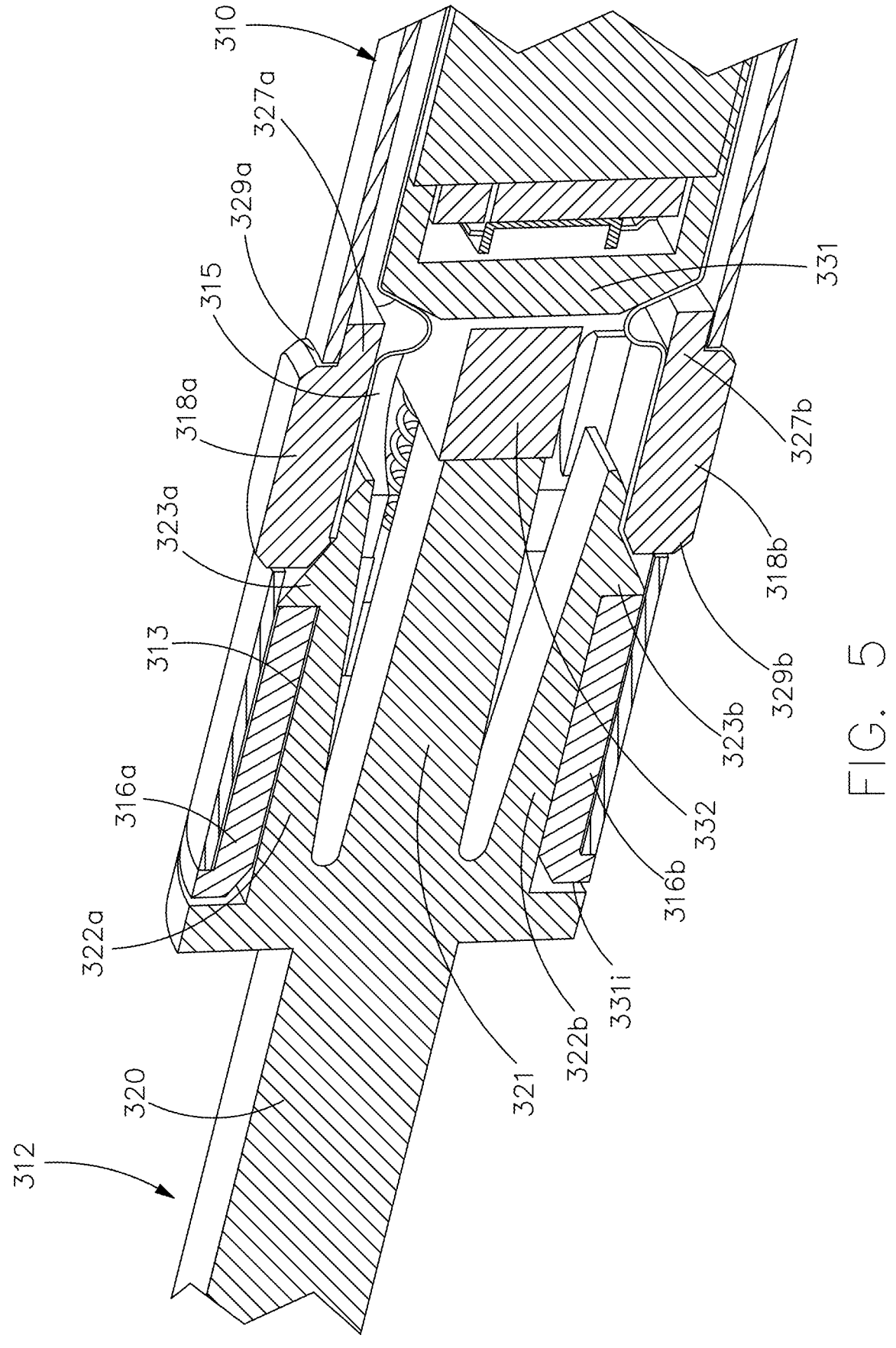
FIG. 5 is a perspective partial view of an interior housing unit, a sharps blade unit and a hollow scalpel handle according to one embodiment of the invention.

In one embodiment, as seen in FIGS. 3, 4 and 5, internal housing unit 315 having interior cavity 313 can be inserted into a hollow handle 310 in permanent attachment. In this embodiment, internal housing unit 315 comprises an upper engagement release arm 327a and lower engagement release arm 327b disposed on opposing sides of its surface that terminate at upper release button 318a and lower release button 318b, each of which extends through upper release hole 329a and lower release hole 329b through surface of scalpel hollow handle 310 to the exterior environment. An upper engagement portion 316a and a lower engagement portion 316b are disposed on opposing sides of the surface of internal housing unit 315. Upper engagement release arm 327a and lower engagement release arm 327b flex inwardly into cavity 313 by depression of upper release button 318a and lower release button 318b. One or more springs 330ᵢ are attached to a surface 331 that is disposed in cavity 313 such that the one or more springs 330ᵢ are oriented along the longitudinal axis of internal housing unit 315. One or more springs 330 may be positioned within cavity 313 as necessary or desired to accommodate other components within cavity 313. In one embodiment, one or more springs 330 are disposed off-center of a longitudinal axis of internal housing unit 315 to permit circuitry and illumination units. In one embodiment, one or more springs 330ᵢ are in direct communication with spring block 332 which is in direct communication with central arm 321. In one embodiment, one or more springs 330ᵢ directly communicate with central arm 321 or other components of scalpel blade unit 312. Internal housing 315 comprises upper cavity hole 339a and lower cavity hole 339b. Internal housing unit 315 comprises keyhole 356 at proximal end 311 distal from distal end 314.

Various components such as illumination sources, electronics and circuitry 350i can be inserted in distal end 314 of cavity 313 of internal housing unit 315. In one embodiment, electronics and circuitry 350i are in permanent attachment with internal housing unit 315. One or more springs 330ᵢ are disposed in cavity 313 along the longitudinal axis of internal housing unit 315. In one embodiment, one or more guide pins 332i may be disposed, partially or entirely, within cavity 313 to stabilize the position of the one or more springs 330ᵢ. In one embodiment, internal housing unit 315 may comprise one or more units, each of which may house various components.

Scalpel blade unit 312 for use with internal housing unit 315 comprises a scalpel blade (not shown) in permanent attachment to the end of scalpel blade unit 312 distal from interior housing unit 315. Scalpel blade unit 312 may comprise a removable guard on the scalpel blade (not shown) that can be removed after scalpel blade unit 312 is attached to interior housing unit 315. Central arm 321 extends from scalpel blade unit 312 proximal to interior housing unit 315 and mates inside of keyhole 356 of interior housing unit 10. Upper arm 322a and lower arm 322b extend from scalpel blade unit 312 proximal to interior housing unit 315. Upper arm 322a comprises an upper arm shoulder 323a and lower arm 322b comprises a lower arm shoulder 323b. Upper arm shoulder 323a extends upward away from central arm 321 and comprises an angled face angling downward toward central arm 321 on the end of upper arm 322a proximate interior housing unit 315. Lower arm shoulder 323b extends downward away from central arm 321 and comprises an angled face angling upward toward central arm 321 on the end of lower arm 322b proximate interior housing unit 315. Upper arm 322a and lower arm 322b are flexibly attached to scalpel blade unit 312.

Upon initial assembly prior to operation, personnel inserts interior housing unit 315 inside of a hollow handle 310 to the point that upper release hole 329a and lower release hole 329b through surface of scalpel hollow scalpel handle 310 are aligned with upper cavity hole 339a and lower cavity hole 339b. Internal housing unit 315 can be attached to the interior of hollow handle 310 in any manner now known or later developed. In one embodiment, internal housing unit 315 is in permanent attachment to the interior of hollow handle 310. In one embodiment, internal housing unit 315 is fixated and attached to the interior of hollow handle 310 through a series of projection tabs (not shown) disposed on the exterior of interior housing unit 315 that mate with series of slots (not shown) in hollow handle 310 to be fixated in a non-movable position withing the interior of hollow handle 310. In one embodiment, internal housing unit 315 is releasably attached to the interior of hollow scalpel handle. Central arm 321, upper arm 322a and lower arm 322b of scalpel blade unit 312 are inserted into keyhole 356 of interior housing unit. Each of upper arm 322a and lower arm 322b have a length longer than upper engagement portion 316a and lower engagement portion 316b. Upper arm 322a and lower arm 322b are inserted into cavity 313 along engagement portion 316a and lower engagement portion 316b wherein upper arm 322a and lower arm 322b flex inwardly due to forces exerted by shoulders 323a, 323b as they travel along engagement portion 316a and lower engagement portion 316b. Once shoulders 323a, 323b have traveled past the ends of upper engagement portion 316a and lower engagement portion 316b that are distal from proximal end 311, the forces exerted by shoulders 323a, 323b are released, causing the angled faces of upper arm and lower arm shoulders 323a, 323b to mate with the angled faces of upper and lower engagement release arms 327a, 327b, causing the angled faces of upper arm and lower arm shoulders 323a, 323b to mate with upper release hole 329a and lower release hole 329b of interior housing unit 315 and upper cavity hole 339a and lower cavity hole 339b. Central unit 321 engages with one or more springs 330ᵢ, displacing one or more springs 330ᵢ from equilibrium and creating a spring force in each of one or more springs 330 as they are held in a displacement condition. In one embodiment, one or more springs 330ᵢ are in direct communication with a spring block 332 which is in direct communication with central arm 321. In one embodiment, one or more springs 330ᵢ directly communicate with central arm 321 or other components of scalpel unit 312.

To release scalpel blade unit 312 from hollow handle 310, personnel press upper engagement release button 318a and lower engagement release button 318b inward toward cavity 313. This causes the angled faces of upper and lower engagement release arms 327a, 327b to press down on the angled faces of upper arm and lower arm shoulders 323a, 323b such that upper arm and lower arm shoulders 323a, 323b are no longer engaged with the ends of upper and lower engagement portions 316a and 316b. This releases the spring force in the one or more springs 330₁, causing scalpel blade unit 312 to disengage from hollow handle 310, and whereupon scalpel blade unit 312 can be ejected directly into a disposable box.

In one embodiment of the invention, any material may be used as a material of construction of the scalpel handle, hollow scalpel handle, interior housing unit and/or the scalpel blade unit, provided that the material of construction is of sufficient strength and thickness to prevent breakage of the exterior and interior components of the scalpel handle, hollow scalpel handle, interior housing unit and/or the scalpel blade unit. In various embodiments, stainless steel, aluminum and plastic materials of construction may be used alone or in combination.

In certain embodiments, the scalpel handle, hollow scalpel handle, interior housing unit and/or the scalpel blade unit (other than the scalpel blade) can be light transmitting. Circuitry and lighting may be embodied in the cavity of the scalpel handle or interior housing unit to provide visual light while performing a surgical procedure. Illumination options enable the user of the scalpel handle or interior housing unit to cycle through different wavelengths and colors of light, either for improved visibility and precision or for therapeutic effects of different wavelengths of light. In one embodiment, illumination can be provided that enables synchronous surgical cutting or mechanical exfoliation of the skin with the therapeutic application of different wavelengths of light, red light (approx. 630-700 nm) for anti-aging effects; blue light (400-470 nm) for anti-acne effects; green light (470-550 nm) to reduce inflammation, calm the skin and possibly lighten pigmentation; and amplified vision through use of all three to create white light (range 400-700 nm) to improve precision, visualization and illumination. In one embodiment, light is transmitted through and around transparent engagement tabs disposed of within the scalpel handle to enable engagement of the scalpel blade unit as well as ejection of the scalpel blade unit. In one embodiment, light can be transmitted through and around the scalpel blade unit.

Any method of illumination can be used that does not interfere with the scalpel blade ejector mechanism. Non-limiting examples of illumination of a scalpel handle and a bayonet can be found in U.S. Pat. Nos. 10,610,257 and 11,925,384 to Hacker.

Although the invention has been described in detail with particular reference to certain exemplary embodiments, various modifications may be made to it by one skilled in the art which will fall within the scope and spirit of the present invention as set forth in the appended claims.

What is claimed is:

1. A sharps blade ejector mechanism comprising:
a handle, the handle defined by a surface, the surface defining a cavity, the handle comprising a proximal end; and
a sharps blade unit, the sharps blade unit comprising a sharps blade in permanent attachment to the sharps blade unit, wherein the handle comprises:
an upper engagement portion and a lower engagement portion disposed on opposing sides of an interior of the surface, wherein the upper engagement portion and the lower engagement portion extend along the interior of the surface from the proximal end of the handle to a position X distal from the proximal end of the handle, wherein the ends of the upper engagement portion and a lower engagement portion at position X each form a ledge vertical to the longitudinal axis of the handle;
an upper release hole and a lower release hole disposed on opposing sides of the interior of the surface that extend through the surface of the handle to the exterior environment, wherein the upper release hole and the lower release hole each extend parallel to the longitudinal axis of the handle beginning at position X to position X distal from the proximal end of the handle;
an upper engagement release arm and a lower engagement release arm disposed on opposing sides of the interior of the surface, wherein the upper engagement release arm and lower engagement release arm extend along the inside of the surface from position X to a point distal from the proximal end of the handle, wherein the upper engagement release arm comprises an upper release button and the lower engagement release arm comprises a lower release button, wherein the upper release button is insertable through the upper release hole and the lower release button is insertable through the lower release hole, wherein the upper engagement release arm comprises an upper engagement release angled face and the lower engagement release arm comprises a lower engagement release angled face;
a first side passage and a second side passage on opposite sides of the interior of the surface disposed at a ninety-degree angle to each of the upper engagement portion and the lower engagement portion; and
a surface disposed in the cavity of the handle distal from position X and the proximal end of the handle to which and end of each of one or more springs are attached along a longitudinal axis of the handle,
wherein the sharps blade unit comprises:
a sharps blade in permanent attachment to an end unit;
a central arm that extends perpendicularly from one side of the end unit along the longitudinal axis of the sharps blade unit; and
an upper arm and a lower arm, each of which extends perpendicularly from the same side of the end unit as the central arm along the longitudinal axis of the sharps blade unit and parallel to the central arm, wherein the upper arm comprises an upper arm shoulder and the lower arm comprises a lower arm shoulder, wherein each of the upper arm shoulder and the lower arm shoulder extends in a direction opposite from the central arm, wherein an end of the upper arm distal from the end unit comprises an upper arm angled face that extends in a direction opposite to the central arm and an end of the lower arm distal from the end unit comprises a lower arm angled face that extends in a direction opposite to the central arm,
wherein the central arm of the sharps blade unit releasably mates within the first side portion and the second side portion of the handle,
wherein the upper arm of the sharps blade unit and the lower arm of the sharps blade unit each releasably extend inside the cavity of the handle whereupon the upper arm shoulder of the upper arm of the sharps blade unit and the lower arm shoulder of the lower arm of the sharps blade unit causing each of the upper arm of the sharps blade unit and the lower arm of the sharps blade unit to flex downwardly inside the cavity of the handle, wherein the upper arm shoulder of the upper arm of the sharps blade unit and the lower arm shoulder of the lower arm of the sharps blade unit extend beyond position X and thereupon flex upwardly inside the cavity whereupon the upper arm shoulder of the upper arm of the sharps blade unit and the lower arm shoulder of the lower arm of the sharps blade unit engage with the ledges formed by each of the upper engagement portion and a lower engagement portion,
wherein the central arm engages with the one or more springs, displacing the one or more springs from equilibrium and creating a spring force in each of the one or more springs.

2. The sharps blade ejector mechanism of claim 1, wherein the sharps blade of the sharps blade unit comprises a scalpel blade, a needle, a probe, a dissector, an elevator, a saw blade, a retractor or a hook.

3. A method of attaching and ejecting a sharps blade to a handle comprising:
inserting the sharps blade unit of claim 1 into the handle of claim 1; and thereafter
ejecting the sharps blade unit of claim 1 from the handle of claim 1,
where ejecting the sharps blade unit from the handle comprises:
pressing downward on the upper release button and the lower release button of the handle until the upper arm of the sharps blade unit and the lower arm of the sharps blade unit disengage with the ledges of the upper engagement portion and a lower engagement portion of the handle,
whereupon the spring force in each of the one or more springs is released,
whereupon the sharps blade unit ejects from the cavity of the handle without contact with a user's hands.

4. The method of attaching and ejecting a sharps blade of claim 3, wherein the sharps blade of the sharps blade unit comprises a scalpel blade, a needle, a probe, a dissector, an elevator, a saw blade, a retractor or a hook.

5. The method of attaching and ejecting a sharps blade of claim 3, wherein the handle comprises illumination.

6. The method of attaching and ejecting a sharps blade of claim 3, wherein the sharps blade unit is ejected directly from the handle into a sharps blade disposable receptacle.

7. A sharps blade ejector mechanism comprising:
a hollow handle, the hollow handle comprising a surface defining a handle cavity and having an upper cavity hole and a lower cavity hole;
one or more internal housing units, at least one of the one or more internal housing units comprising:
an interior cavity comprising at least one end open to an exterior environment;
an upper engagement portion and a lower engagement portion disposed on opposing sides of the interior cavity;
a keyhole located at a second end of the internal housing unit open to the exterior environment; and
one or more springs disposed in the interior cavity in a longitudinal direction to the internal housing unit; and
a sharps blade unit comprising:
a sharps blade;
a central arm extending along the longitudinal axis of the sharps blade unit; and
an upper arm and a lower arm extending along the longitudinal axis of the sharps blade unit, wherein the upper arm extends above the central arm and the lower arm extends below the central arm, wherein the upper arm comprises an upper release button and the lower arm comprises a lower button;
wherein the one or more internal housing units are disposed into the handle cavity,
wherein the central arm, upper arm and lower arm of the sharps blade unit are disposed in the interior cavity of the one or more interior housing units through the keyhole until the central arm mates with one or more of the one or more springs, the upper arm release button mates with the upper cavity hole of the hollow handle and the lower arm release button mates with the and a lower cavity hole of the hollow handle.

8. The sharps blade ejector mechanism of claim 7, wherein one or more of the sharps blade unit, the hollow handle and the one or more interior housing units are light transmissible.

9. The sharps blade ejector mechanism of claim 7, wherein one or more of an illumination source, electronic circuitry and power source are disposed into the interior cavity at the distal end through one of the one or more interior housing units.

10. The sharps blade ejector mechanism of claim 9, wherein the electronic circuitry is in communication with one or more illumination source, wherein the electronic circuitry is programmed to permit the one or more illumination source to cycle through different wavelengths and colors of light.

11. The sharps blade ejector mechanism of claim 10, wherein the light comprises red light at approximately 630-700 nm wavelength, blue light at approximately 400-470 nm wavelength, green light at approximately 470-550 nm wavelength, or white light at approximately 400-700 nm wavelength.

12. The sharps blade ejector mechanism of claim 11, wherein the illumination source is powered by one or more batteries.

13. The sharps blade ejector mechanism of claim 12, wherein the one or more batteries are rechargeable.

14. The sharps blade ejector mechanism of claim 9, wherein the electronic circuitry is programmed to communicate to a computer server via wireless technology.

15. The sharps blade ejector mechanism of claim 9, wherein the cavity of the handle comprises circuitry to record video or take photographs.

16. The sharps blade ejector mechanism of claim 7, wherein the sharps blade unit is disposable.

17. The sharps blade ejector mechanism of claim 7, wherein the sharps blade unit is reusable.

18. The sharps blade ejector mechanism of claim 7, further comprising a removable sharps blade guard covering the sharps blade.

19. The sharps blade ejector mechanism of claim 7, wherein the hollow handle is reusable.

20. The sharps blade ejector mechanism of claim 7, wherein the hollow handle comprises stainless steel, aluminum, plastic or combinations thereof.

21. The sharps blade ejector mechanism of claim 7, wherein the sharps blade unit comprises stainless steel, aluminum, plastic or combinations thereof.

22. The sharps blade ejector mechanism of claim 7, wherein the sharps blade of the sharps blade unit comprises a scalpel blade, a needle, a probe, a dissector, an elevator, a saw blade, a retractor or a hook.

23. A method of attaching and ejecting a sharps blade to a handle comprising:

inserting the sharps blade unit of claim 7 into the one or more interior housing units of claim 7;

inserting the one or more interior housing units of claim 7 into the hollow handle of claim 7; and thereafter ejecting the sharps blade unit from the hollow handle of claim 7, where ejecting the sharps blade unit from the hollow handle comprises:

pressing downward on the upper release button and the lower release button of the hollow handle until the upper arm of the sharps blade unit and the lower arm of the sharps blade unit disengage with the upper engagement portion and the lower engagement portion of the interior housing unit, whereupon the spring force in each of the one or more springs is released, whereupon the sharps blade unit ejects from the cavity of the hollow handle without contact with a user's hands.

* * * * *